United States Patent [19]

Nikles et al.

[11] 3,933,858

[45] Jan. 20, 1976

[54] PHENYL CARBAMATES

[75] Inventors: Erwin Nikles, Liestal; Volker Dittrich; Ladislaus Pinter, both of Basel, all of Switzerland

[73] Assignee: Ciba-Geigy AG, Basel, Switzerland

[22] Filed: Oct. 10, 1974

[21] Appl. No.: 513,607

Related U.S. Application Data

[60] Division of Ser. No. 402,650, Oct. 1, 1973, Pat. No. 3,856,816, which is a division of Ser. No. 197,474, Nov. 10, 1971, Pat. No. 3,781,301, which is a continuation of Ser. No. 2,445, Jan. 12, 1970, abandoned, which is a continuation-in-part of Ser. No. 782,335, May 13, 1968, abandoned, which is a division of Ser. No. 493,256, Oct. 5, 1965, abandoned.

[30] Foreign Application Priority Data

Oct. 8, 1964  Switzerland.................. 13113/64

[52] U.S. Cl. ............................................. 260/340.7
[51] Int. Cl.² ...................................... C07D 319/06

[58] Field of Search .................................. 260/340.7

[56] References Cited

UNITED STATES PATENTS 3,781,301  12/1973  Nikles et al.................. 260/340.7 X Primary Examiner—Anton H. Sutto
Attorney, Agent, or Firm—Frederick H. Rabin

[57] ABSTRACT

O-Phenylcarbamates, e.g. those of the formula

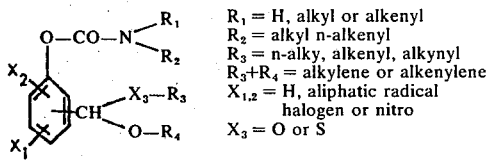

$R_1$ = H, alkyl or alkenyl
$R_2$ = alkyl n-alkenyl
$R_3$ = n-alky, alkenyl, alkynyl
$R_3+R_4$ = alkylene or alkenylene
$X_{1,2}$ = H, aliphatic radical halogen or nitro
$X_3$ = O or S are biocides, e.g. insecticides.

1 Claim, No Drawings

PHENYL CARBAMATES

CROSS REFERENCES TO RELATED APPLICATIONS

This is a division of application Ser. No. 402,650, filed on Oct. 1, 1973, now U.S. Pat. No. 3,856,816, which is a division of application Ser. No. 197,474, filed on Nov. 10, 1971, now U.S. Pat. No. 3,781,301. Application Ser. No. 197,474 is a continuation of application Ser. No. 2,445 filed on Jan. 12, 1970, which in turn was a continuation-in-part of application Ser. No. 782,335 filed on May 13, 1968, which in turn was a division of application Ser. No. 493,256 filed on Oct. 5, 1965, all of which are now abandoned.

SUMMARY OF THE INVENTION

The present invention concerns and has for its object the provision of new O-phenyl-carbamates of Formula I

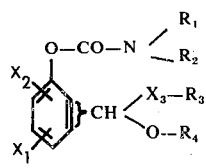

in which each of $R_1$ and $R_2$ is hydrogen, lower alkyl or lower alkenyl, each of $X_1$ and $X_2$ is hydrogen, a saturated or unsaturated lower aliphatic radical, halogeno or nitro, $X_3$ is oxygen or sulfur and each of $R_3$ and $R_4$ are alkyl, alkenyl or alkynyl or, when taken together, represent alkylene or alkylene forming with the remaining moiety a 5 to 7 membered heterocycle, and in which $R_3$ and $R_4$ are unsubstituted or substituted by lower aliphatic radicals, halogeno, nitro or free or etherified hydroxy or mercapto, as well as of corresponding pesticidal preparations and methods for the preparation and application of these products. Said preparations are useful in the control of a wide variety of vegetable and animal pests.

DESCRIPTION OF THE PREFERRED EMBODIMENT

The radicals $R_1$ and $R_2$ are identical or different and represent, for example, hydrogen, methyl, ethyl n- or i-propyl or allyl.

The moiety

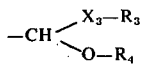

in o- or m- position results from reacting the corresponding aldehyde, semiacetal or semimercaptal, for example, with methanol, ethanol, propanol, isopropanol, allyl alcohol, propargyl alcohol, 2-methoxyethanol, 2-methylmercaptoethanol, 2-chlorethanol, 2-bromethanol or 2-hydroxyethanethiol, or the corresponding semiacetal with methylmercaptan, ethylmercaptan, n-propylmercaptan, isopropylmercaptan, n-butylmercaptan, allylmercaptan, chlorallylmercaptan, dichlorallylmercaptan, propargylmercaptan, 2-methoxyethanethiol, or 2-methylmercaptoethanethiol. In case $R_3$ and $R_4$, when taken together, represent alkylene or alkenylene, said moiety results from the reaction of the corresponding aldehyde, for example, with racemic 1,2-propanediol, (+)(S)-1,2-propanediol, (−)(R)-1,2-propanediol, 3-fluoro-1,2-propanediol, 3-chloro-1,2-propanediol, 3-bromo-1,2-propanediol, 3-iodo-1,2-propanediol, 3-methoxy-1,2-propanediol, 3-ethoxy-1,2-propanediol, 3-isopropoxy-1,2-propanediol, 3-allyloxy-1,2-propanediol, 3-methallyloxy-1,2-propanediol, 3-propargyloxy-1,2-propanediol, 3-acetoxy-1,2-propanediol, 3-methylmercapto-1,2-propanediol, 3-chlorallylmercapto-1,2-propanediol, glycerol, 1,3-propanediol, 2-chloro-1,3-propanediol, 2-bromo-1,3-propanediol, 2-nitro-1,3-propanediol, (+)(R)-1,2-butanediol, (−)(S)-1,2-butanediol, racemic 1,2-butanediol, 1,3-butanediol, 1,4-butanediol, meso-2,3-butanediol, (−)(2R:3R)-2,3-butanediol, (+)(2S:3S)-2,3-butanediol, 1-butene-3,4-diol, 2-butene-1,4-diol, 2-hydroxymethyl-2-propen-1-ol, 2-hydroxymethyl-2-buten-1-ol, 2-methyl-1,2-propanediol, 3-chloro-2-methyl-1,2-propanediol, 3-chloro-2-chloromethyl-1,2-propanediol, 2-methyl-1,3-propanediol, 2-nitro-2-methyl-1,3-propanediol, 1,2-pentanediol, 1,3-pentanediol, 2,3-pentanediol, 2,4-pentanediol, 1-pentene-3,4-diol, 2-methyl-1,2-butanediol, 2-methyl-1,3-butanediol, 2-methyl-2,3-butanediol, 2-methyl-2,4-butanediol, 2-methyl-3,4-butanediol, 2-ethyl-1,3-propanediol, 1,4-dichloro-2-methyl-2,3-butanediol, 4-bromo-2-methyl-2,3-butanediol, 4-iodo-2-methyl-2,3-butanediol, 2,2-dimethyl-1,3-propanediol, 2,2-bischloromethyl-1,3-propanediol, 2,4-hexanediol, 2-methyl-2,3-pentanediol, 3-methyl-2,4-pentanediol, 2,2-dimethyl-3,4-butanediol, 1,5-hexadiene-3,4-diol, 2-ethanol-1-thiol, 2-propanol-1-thiol, 3-chloro- 2-propanol-1-thiol, 3-propanol-1-thiol. Accordingly, each of $R_3$ and $R_4$ is preferably lower alkyl, lower alkenyl, lower alkynyl, lower alkoxy-lower alkyl, lower alkylmercapto-lower alkyl, halo-lower alkyl, hydroxy-lower alkyl, halo-lower alkenyl, or $R_3$ and $R_4$, when taken together, preferably lower alkylene, mono- or di-halo-lower alkylene, lower alkoxy-lower alkylene, lower alkenyloxy-lower alkylene, lower alkynyloxy-lower alkylene, lower alkanoyloxy-lower alkylene, lower alkylmercapto-lower alkylene, halo-lower alkenylmercapto-lower alkylene, hydroxy-lower alkylene, nitro-lower alkylene, lower alkenylene, hydroxy-lower alkenylene or lower alkadienylene. The term "lower" referred to above and hereinafter in connection with organic radicals or compounds respectively, defines such with up to 6 carbon atoms.

The radicals $X_1$ and $X_2$ are identical or different and represent, for example, hydrogen, lower alkyl, e.g. methyl, lower alkoxy, alkenyloxy or alkynyloxy or -mercapto or haloalkenylmercapto, e.g. methoxy, isopropoxy, allyloxy, propargyloxy, methylmercapto, allylmercapto or chlorallylmercapto, halogeno, e.g. fluoro, chloro, bromo or iodo, trifluoromethyl, nitro, di-lower alkylamino or di-lower alkenylamino. In this series most preferred compounds are obtained when $X_1$ and $X_2$ each represents a hydrogen atom, a lower alkyl or a lower alkoxy radical. Accordingly, the above mentioned aldehydes, represent, for example, salicylaldehyde, 4-methyl salicylaldehyde, 5-methyl-salicylaldehyde, 4-methoxy-salicylaldehyde, 4-isopropoxy-salicylaldehyde, 4-chloro-salicylaldehyde, 5-chloro-salicylaldehyde, 5-bromo-salicylaldehyde, 5-methylmercapto-salicylaldehyde, 4-trifluoromethyl-salicylaldehyde, 5-nitro-salicylaldehyde, 4-dimethylamino-salicylaldehyde, 3,5-dichloro-salicylaldehyde, 3,5-dinitro-salicylaldehyde, 3-hydroxybenzaldehyde, 2-chloro-3-hydroxybenzaldehyde, 6-bromo-3- hydroxybenzaldehyde or 5-hydroxy-3-methylbenzaldehyde.

The compounds of the invention exhibit valuable properties, for example, biocidal, especially insecticidal and acaricidal properties. Furthermore, they act also as herbicides, bactericides, fungicides and molluscicides. Inter alia, these carbamates develop a very strong action, for example, against houseflies, aphids, caterpillars and beetles, for example, corn weavil and Colorado beetle. Their contact effect is far superior to that of the known active substance "Carbaryl" (N-methyl-α-naphthylcarbamate).

They are not only suitable for use as herbicides, but when applied in a concentration that does not produce phytotoxic effects, they may also be used in plant protection since they develop an excellent effect against harmful microorganisms, for example against fungi, for example *Alternaria solani, Phytopthora infestans* and *Septoria apii*, as well as against harmful insects, acarides, nematodes and their ova and larvae. The may also be used quite generally as microbicides, for example, against Aspergillus species.

Particularly useful are compounds of Formula I in which each of $R_1$ and $R_2$ is hydrogen, lower alkyl or lower alkenyl, each of $X_1$ and $X_2$ is hydrogen, lower alkyl, lower alkoxy, lower alkenyloxy, lower alkynyloxy, lower alkylmercapto, lower alkenylmercapto, lower alkynylmercapto, lower haloalkenylmercapto, halogeno, trifluoromethyl, nitro, di-lower alkylamino or di-lower alkenylamino, $X_3$ is oxygen or sulfur and each of $R_3$ and $R_4$ is lower alkyl, lower alkenyl, lower alkynyl, lower alkoxy-lower alkyl, lower alkylmercapto-lower alkyl, halo-lower alkyl, hydroxy-lower alkyl, halo-lower alkenyl or $R_3$ and $R_4$, when taken together, represent lower alkylene, mono- or di-halo-lower alkylene, lower alkoxy-lower alkylene, lower alkenyloxy-lower alkylene, lower alkynyloxy-lower alkylene, lower alkanoyloxy-lower alkylene, lower alkylmercapto-lower alkylene, halo-lower alkenylmercapto-lower alkylene, hydroxy-lower alkylene, nitro-lower alkylene, lower alkenylene, hydroxy-lower alkenylene or lower alkadienylene, forming with the remaining moiety a 5 to 7 membered heterocycle.

Especially suitable for insect control are the carbamates of Formula I wherein $R_1$ is hydrogen, $R_2$ is lower alkyl, each of $X_1$ and $X_2$ is hydrogen, methyl, chloro, bromo, trifluoromethyl or nitro, $X_3$ is oxygen or sulfur and each of $R_3$ and $R_4$ is lower alkyl, lower alkenyl or lower alkynyl or $R_3$ and $R_4$, when taken together represent alkylene or alkenylene with 2 to 4 carbon atoms, forming with the remaining moiety a 5 to 7 membered hetereocycle and being unsubstituted or substituted by halogen, nitro, hydroxy, lower alkoxy or lower alkenyloxy.

Preferred are compounds of Formulae II and III

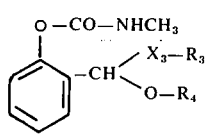

II

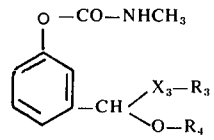

III in which $X_3$ is oxygen or sulfur and each of $R_3$ and $R_4$ is lower alkyl, lower alkenyl or lower alkynyl or $R_3$ and $R_4$, when taken together, represent alkylene or alkenylene with 2 to 4 carbon atoms, forming with the remaining moiety a 5 to 7 membered heterocycle and being unsubstituted or substituted by halogen, nitro, hydroxy, lower alkoxy or lower alkenyloxy.

Most preferred are compounds of the formula II in which $X_3$ is oxygen or sulfur and each of $R_3$ and $R_4$ is lower alkyl or $R_3$ and $R_4$, when taken together, represent alkylene or alkenylene with 2 to 4 carbon atoms, forming with the remaining moiety a 5 to 7 membered unsubstituted heterocycle and of Formula IV

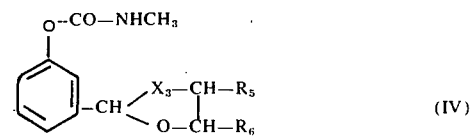

in which $X_3$ is oxygen or sulfur and each of $R_5$ and $R_6$ is hydrogen or lower alkyl.

Outstanding are the compounds of Formula IV, in which $X_3$ is oxygen or sulfur and each of $R_5$ and $R_6$ is hydrogen or methyl.

The compounds of the invention are prepared, for example, by reacting a phenol of the formula V

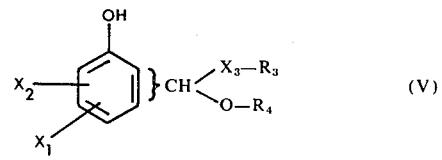

with a reactive derivative of carbonic acid and with $R_1$—NH—$R_2$.

The reaction of the phenol with the reactive derivative of carbonic acid and the amine may be carried out in either sequence, depending to some extent on the constitution of the required final product. Accordingly, said phenol or an alkali metal salt thereof may be reacted, for example, with phosgene and the resulting chlorocarbonate or carbonate condensed with $R_1$—NH—$R_2$.

Alternatively, said amine may be first reacted with phosgene and the resulting carbamic acid chloride or (when $R_1$ or $R_2$ represents hydrogen) the isocyanate readily formed from it, may be reacted with the phenol. Furthermore, a urethane derived from the amine, preferably an alkyl urethane, may be reacted with the phenol (transesterification). It is also possible to react an urea derived from the amine with the phenol preferably at a raised temperature.

The products so obtained are open-chain or cyclic acetals or mercaptals, depending on the stoichiometric proportions of the starting materials and on the valency of the alcohols or mercaptans. According to the size of the ring and the kind of hetero atom present in the acetalized moiety, the carbamates of this invention may be designated as derivatives of 1,3-dioxolan (from 1,2-glycols), of 1,3-dioxan (from 1,3-glycols), of 1,3-dioxeen (from 1,4-glycols) or 1,3-oxathiolans (from 1,2-hydroxymercaptans).

The starting materials used are known or, if new, can be prepared analogous to the method for the known products (cf. for example Houben-Weyl, Methoden der organischen Chemie, volume 2, part 1, Stuttgart 1945). For example, the phenols of Formula V are prepared by reacting an ortho- or meta-hydroxy-benzaldehyde with a lower alcohol or mercaptan in the presence of an acid catalyst, for example zinc chloride, a mineral acid or paratoluenesulphonic acid. These reactions may also be carried out with aldehyde derivatives, for example oximes, aldehydanils or acetals (transacetalization). Another suitable route is the acetalization with the aid of ortho-formic acid esters, formimine ethers, dimethylsulphite or ortho-silicic acid esters in the presence of lower aliphatic alcohols. Another route leading to said phenols is the reaction of suitable halides with alkali metal or alkaline earth metal alcoholates.

Said acetalization may be performed in two stages, with the semiacetals or semimercaptals being formed in the first reaction stage. When different alcohols are used in the two reaction stages, mixed acetals, i.e. monothioacetals, are obtained.

When optically active alcohols or mercaptans are used, there may be prepared optically active phenols of the Formula V and from them optically active carbamates of the Formula I. If its acetal moiety is cyclic and substituted, further isomerizing possibilities offer themselves. A carbamate of the Formula I whose acetal residue is monosubstituted may be obtained in the cis-form or trans-form. In general, the present process for the manufacture of said carbamates gives rise to mixtures of all possible isomers; these mixtures can be separated into their constituents by known methods, for example by crystallization. For the manufacture of the preparations of this invention to be used for pest control, however, the stereoisomer mixtures obtained in the manufacture of the active substances are generally used. As mentioned in the beginning the present invention also provides pesticidal preparations comprising as the active ingredient at least one carbamate of the Formula I and, if desired, one of the following additives. Such additives are those commonly used in pesticidal preparations such as vehicles, solvents, diluents, dispersants, wetting agents, adhesives, fertilizers and, if required, further pesticides. Corresponding spray solutions are prepared, for example, with petroleum fractions having a high to medium boiling range, for example Diesel oil or kerosene, coal tar oil, or oils of vegetable or animal origin, as well as hydrocarbons, for example alkylated naphthalenes, tetrahydronaphthalene, if desired or required with the use of xylene mixtures, cyclohexanols ketones or chlorinated hydrocarbons for example trichloroethane or tetrachloroethane, trichloroethylene or tri- or tetrachlorobenzenes. It is advantageous to use organic solvents having a boiling point above 100°C.

It is especially advantageous to prepare aqueous forms of application from emulsion concentrates, pastes or wettable spray powders by addition of water. Suitable emulsifiers or dispersants are non-ionic products, for example condensation products of aliphatic alcohols, amines or carboxylic acids with a long-chain hydrocarbon residue of about 10 to 20 carbon atoms with ethylene oxide, for example the condensation product from octadecyl alcohol with 25 to 30 mols of ethylene oxide, or of commercial oleylamine with 15 mols of ethylene oxide, or of dodecylmercaptan with 12 mols of ethylene oxide. As suitable anionic emulsifiers, there may be mentioned the following: The sodium salt of dodecylbenzosulphonic acid, the potassium of triethanolamine salt of oleic acid or of abietic acid or of a mixture of these two acids, or the sodium salt of a petroleumsulphonic acid. Suitable cationic dispersants are quaternary ammonium compounds, for example cetyl pyridinium bromide and dihydroxyethyl benzyl dodecyl ammonium chloride.

For the manufacture of dusting and casting preparations, there may be used as solid vehicles:- talcum, kaolin, bentonite, calcium carbonate, calcium phosphate or coal, cork meal, wood meal or other materials of vegetable origin. It is also very advantageous to manufacture the preparations in the form of granulates. The various forms of application may contain the conventional additives that improve the distribution, the adhesion, stability to rain or the penetration; as such substances there may be mentioned fatty acids, resin, glue, casein and alginates.

The preparations of this invention may be used by themselves or in conjunction or admixture with conventional pesticides, especially insecticides, acaricides, nematocides, bactericides, fungicides, herbicides and the like.

The following Examples are intended to illustrate the invention and are not to be construed as being limitations thereon. Temperatures are given in degrees Centigrade, and all parts or percentages wherever given are such by weight.

EXAMPLE 1 a. ortho-(1,3-dioxolan-2-yl)-phenol

A mixture of 244 parts of salicylaldehyde, 125 parts of ethyleneglycol, 1 part of zinc chloride, 1 part by volume of concentrated phosphoric acid and 500 parts by volume of benzene was boiled in a circulating distillation apparatus until water was no longer being eliminated. The solution of the product was filtered and evaporated. The residue was distilled under a high vacuum. The product boiled at 88° to 91°C under 0.04 mm Hg pressure and melted at 67° to 70°C.

b. ortho-(1,3-dioxolan-2-yl)-phenyl-N-methyl-carbamate

A solution of 50 parts of ortho-(1,3-dioxolan-2-yl)-phenol in 300 parts by volume of dry toluene was mixed with about 0.2 part by volume of triethylamine, and 20 parts of methylisocyanate were dropped into this solution at room temperature. The temperature rose gradually to 31°C. The mixture was kept for 1 day at room temperature. The product was filtered off and crystallized from toluene; it melted at 111° to 114°C.

EXAMPLE 2

When glycols (polyols) were reacted with unsubstituted or substituted ortho- or meta-hydroxybenzaldehyde, the condensation as described in Example 1 lead to cyclic acetals. When these acetals were reacted with methylisocyanate, they furnished, for example, the following carbamates:

| No. | Aldehyde | Glycol | Cyclic acetal | Carbamate |
|---|---|---|---|---|
| 1 | salicylaldehyde | 1,2-propanediol | b.p.85°C/0.03mm Hg | ortho-(4-methyl-1,3-dioxolan-2-yl)-phenyl-N-methyl-carbamate (crystallizes gradually) |
| 2 | " | 2,3-butanediol (commercial mixture of stereoisomers) | b.p.86°C/0.07mm Hg | ortho-(4,5-dimethyl-1,3-dioxolan-2-yl)-phenyl-N-methyl-carbamate, m.p. 70 – 105°C |
| 3 | " | 1-butane-3,4-diol | b.p.82°C/0.08mm Hg | ortho-(4-vinyl-1,3-dioxolan-2-yl)-phenyl-N-methyl-carbamate |
| 4 | " | glycerol-α-monochlorohydrin | b.p.111 – 114°C 0.3mm Hg | ortho-(4-chloromethyl-1,3-dioxolan-2-yl)-phenyl-N-methyl-carbamate, m.p. about 30 to 70°C |
| 5 | " | glycerol | m.p.148 to 149°C from acetonitrile | ortho-(4-hydroxymethyl-1,3-dioxolan-2-yl)-phenyl-N-methyl-carbamate, or ortho-(5-hydroxy-1,3-dioxan-2-yl)-phenyl-N-methyl-carbamate, m.p.130 to 134°C. As by-product the corresponding bis-N-methyl-carbamate melting at 170 to 172°C was obtained. |
| 6 | " | 1,3-propanediol | b.p.92 to 96°C 0.01mm Hg | ortho-(1,3-dioxan-2-yl)-phenyl-M-methyl-carbamate. M.p.125 to 127°C (from toluene) |
| 7 | " | 1,3-butanediol | b.p.89 to 95°C 0.06mm Hg | ortho-(4-methyl-1,3-dioxan-2-yl)-phenyl-N-methyl-carbamate, b.p.146 to 148°C (from acetonitrile) |
| 8 | " | neopentylglycol | b.p.90°C/0.06mm Hg - m.p.58 – 60°C | ortho-(5,5-dimethyl-1,3-dioxan-2-yl)-phenyl-N-methyl-carbamate, b.p.122 to 124°C (from carbon tetrachloride) |
| 9 | " | 3-methyl-2,4-pentandediol | b.p.93°C/0.01mm Hg | ortho-(4,5,6-trimethyl-1,3-dioxan-2-yl)-phenyl-N-methyl-carbamate m.p. 118 to 136°C |
| 10 | " | 2-methyl-2-nitro-1,3-propanediol | m.p.90 to 93°C (from ether+cyclohexane) | ortho-(5-methyl-5-nitro-1,3-dioxan-2-yl)-phenyl-N-methyl-carbamate m.p.131 – 133°C (from isopropanol) |
| 11 | " | 2-butene-1,4-diol | b.p.87°C/0.03mm Hg | ortho-(1,3-dioxep-5-en-2-yl)-phenyl-N-methyl-carbamate m.p.94 – 95°C (from toluene) |
| 12 | 4-methylsalicylaldehyde | ethyleneglycol | b.p.98°C/0.02mm Hg; crystallizes | ortho-(1,3-dioxolan-2-yl)-meta'-methylphenyl-N-methyl-carbamate m.p.96 to 99°C (from toluene) |
| 13 | 5-methylsalicylaldehyde | " | b.p.95 – 96°C 0.01mm Hg | ortho-(1,3-dioxolan-2-yl)-para-methylphenyl-N-methyl-carbamate m.p.104 to 106°C (from carbon tetrachloride) |
| 14 | mixture of 4- and 6-trifluoromethyl-salicylaldehyde +) | 1,2-propanediol | b.p.90°C/0.7mm Hg | ortho-(4-methyl-1,3-dioxolan-2-yl)-meta- and meta'-trifluoromethylphenyl-N-methyl carbamate (viscous oil) |
| 15 | 5-chlorosalicylaldehyde | ethyleneglycol | m.p.82°C (from toluene) | para-chloro-ortho-(1,3-dioxolan-2-yl)-phenyl-N-methyl carbamate m.p.109 – 112°C (from benzene+hexane) |
| 16 | mixture of 4- and 6-chlorosalicylaldehyde | 1,2-propanediol | b.p.93 – 98°C/0.01mm Hg | ortho-(4-methyl-1,3-dioxolan-2-yl)-meta- and meta'-chlorophenyl-N-methyl carbamate, m.p. about 90 to 100°C |
| 17 | 5-bromosalicylaldehyde | ethyleneglycol | m.p.81°C (from hexane) | para-bromo-ortho-(1,3-dioxolan-2-yl)-phenyl-N-methyl-carbamate, m.p. 107 to 109°C (from ethylene chloride) |
| 18 | 3,5-dibromo-salicylaldehyde | " | b.p.145°C/0.17mm Hg m.p.60 to 64°C | ortho,para-dibromo-ortho'-(1,3-dioxolan-2-yl)-phenyl-N-methyl-carbamate m.p.135 –139°C (from acetonitrile) |
| 19 | 3,5-dinitrosalicylaldehyde | " | m.p. 134 – 140°C (from chlorobenzene) | ortho,para-dinitro-ortho'-(1,3-dioxolan-2-yl)-phenyl-N-methyl-carbamate m.p.149 – 155°C (from acetone) |
| 20 | meta-hydroxybenzaldehyde | " | b.p.113 to 115°C/0.03 mm Hg | meta-(1,3-dioxolan-2-yl)-phenyl-N-methyl-carbamate, m.p.73 to 77°C (from toluene) |
| 21 | meta-hydroxybenzaldehyde | 2,3-butanediol (commercial) | b.p.115°C/0.1mm Hg | meta-(4,5-dimethyl-1,3-dioxolan-2-yl) phenyl-N-methyl-carbamate, viscous oil |

+) 4(6)-trifluoromethyl-salicylaldehyde can be prepared from 3-trifluoromethylphenol by the method of J. C. Duff [J.Chem.Soc. 1941, page 547, Proc.Iowa Acad.Sci.52, page 191 (1945)]. It boils at 77 to 80°C under 14mm Hg pressure.

EXAMPLE 3

Salicylaldehyde diethyl acetal

A mixture of 122 parts of salicylaldehyde, 180 parts of orthoformic acid ethyl ester and 120 parts of anhydrous ethanol was mixed with 1 ml of concentrated hydrochloric acid, whereupon the whole heated up spontaneously. After a short time, the solution was heated to the boil and then evaporated under vacuum, and the residue distilled under a high vacuum. The product passed over at 80°C under 0.15mm Hg pressure.

ortho-(diethoxymethyl)-phenyl-N-methyl-carbamate

A solution of 138 parts of salicylaldehyde diethyl acetal, 46 parts of methylisocyanate and 0.5 part of triethylenediamine in 1,000 parts by volume of dry toluene was kept for 14 hours at room temperature. The resulting crystalline ortho-(diethoxymethyl)-phenyl-N-methyl-carbamate was filtered off, washed with 250 parts by volume of dry toluene and dried under vacuum. It melted at 92° to 93°C.

ortho-(Dimethoxymethyl)-phenyl-N-methyl-carbamate, melting at 62° to 64°C (after crystallization from dibutyl ether), was prepared in a similar manner, starting from salicylaldehyde dimethylacetal.

EXAMPLE 4 ortho-(1,3-oxathiolan-2-yl)-phenol

82 Parts of 2-mercaptoethanol were mixed with 0.5 part by volume of concentrated hydrochloric acid and then dropwise with 122 parts of salicylaldehyde; the temperature of the mixture rose. The reaction mixture was stirred for 1 hour at room temperature, then diluted with 500 parts by volume of ether and washed with sodium bicarbonate solution and then with water until the washings ran neutral. The solution was dried over anhydrous sodium sulphate, filtered and evaporated.

The viscous residue was heated under a high vacuum at a bath temperature of 160°C, and the volatile phase was condensed. The condensate was then fractioned. At 112°C under a pressure of 0.05mmm Hg, the ortho-(1,3-oxathiolan-2-yl)-phenol formed passed over and crystallized on standing. It melted at 72° – 74°C.

ortho-(1,3-oxathiolan-2-yl)-phenyl-N-methyl-carbamate

15 Parts of methylisocyanate and 0.1 part of triethylenediamine were added to a solution of 37 parts of ortho-(1,3-oxathiolan-2-yl)-phenol in 100 parts by volume of dry toluene. The mixture was moderately cooled to maintain its temperature below 35°C. After a few hours, the resulting crystalline product was filtered off and recrystallized from toluene or carbon tetrachloride. It melted at 108° to 109°C.

EXAMPLE 5 ortho,para-dinitro-ortho'-(1,3-dioxolan-2-yl)-phenol

A mixture of 196 parts of 3,5-dinitrosalicylaldehyde, 70 parts of glycol and 500 parts by volume of benzene was boiled in the presence of 1 part of anhydrous zinc chloride and 1 part by volume of concentrated phosphoric acid in a circulation distillation apparatus, until water was no longer being eliminated. After cooling, the product were filtered off and crystallized from chlorobenzene; it melted at 134° to 140°C.

ortho,para-dinitro-ortho'-(1,3-dioxolan-2-yl)-phenol-N,N-dimethyl-carbamate 11.3 Parts of dimethylcarbamic acid chloride were added to a mixture of 25.6 parts of ortho,para-dinitro-ortho'-(1,3-dioxolan-2-yl)-phenol, 200 parts by volume of chlorobenzene and 25 parts of triethylamine. The solution was heated for 5 hours at 130°C, allowed to cool, filtered, washed with 2N-sodium carbonate solution and evaporated. The residue was crystallized from alcohol. The product melted at 141° to 142°C.

EXAMPLE 6

Dusting Agent

Equal parts of an active substance described in Examples 1 to 5 were mixed with precipitated silica and finely ground. When this powder is mixed with kaolin or talcum, it may be used in the form of dusting preparations having the desired concentration of active substance. In general, preparations containing 1 to 5% of active substance are preferred.

Spray Powder

To manufacture a spray powder, the following ingredients, for example, were mixed and then finely ground:
50 parts of an active substance of Examples 1 to 5
20 parts of Hisil (highly adsorbent, precipitated silica)
25 parts of bolus alba (kaolin)
3.5 parts of a reaction product from para-tertiary octylphenol and ethylene oxide
1.5 parts of sodium 1-benzyl-2-stearyl-benzimidazole-6,3' - disulphonate.

Emulsion Concentrate

Readily soluble active substances were also formulated in the form of an emulsion concentrate as follows:
20 parts of active substance
70 parts of xylene
10 parts of a mixture of a reaction product of an alkylphenol with ethylene oxide and calcium dodecyl benzenesulphonate
were mixed. On dilution with water to the desired concentration, an emulsion suitable for spraying was obtained.

EXAMPLE 7

The active substance of Example 1 and the active substance "Carbaryl" were subjected to a comparative test to establish their contact effect against houseflies and corn weavils. The new substance displayed a much greater, distinct contact-insecticidal effect.

When applied in a concentration of 0.04% in the control of aphids (aphis fabae) on young bean plants, it was found that after 2 days the active substance of Example 1 had completely destroyed the aphids. It was found to have a good diffusion and distinct systemic effect.

Carbaryl was found to be ineffective in these tests. Carbaryl is the common name for 1-naphthyl-N-methyl-carbamate.

The above-mentioned active substance is active in limit concentrations of 1.2 parts per million against aedes larvae (24 hours).

The compound was also tested in dust form against various pests (1%, $2g/m^2 = 20kg$ per hectare) and the following results were recorded:

|  | after 6 hours | after 24 hours |
|---|---|---|
| Phyllodronia germanica | 100% |  |
| Procellic scaber | 100% |  |
| Formica rufa |  | 100% |

A topical test on larvae of *Periplaneta americana* revealed in an evaluation made 24 hours later the following limit concentrations of active substance compared with various commercially available phosphoric acid esters:

| Phosphoric acid ester | I | 6 | in Γ per pest |
|---|---|---|---|
| " | II | 13 | |
| " | III | 9 | |
| active substance of Example 1 |  | 2 | |

I = O,O-dimethyl-O-(3-methyl-4-nitrophenyl)-thionophosphate
II = O,O-dimethyl-O-(1-chloro-1-N-diethyl-carbaminyl-1-propen-2-yl)-phosphate
III = O,O-dimethyl-O-(4-methylmercapto-3-methylphenyl)-thinophosphate.

The active substance of Example 1 acts also against spider mites (*Tetranychus urticae*).

When tested as a stomach poison on Carausius, the said active substance displayed a good effect, against Prodenia a moderate to good effect and against Gastroidea rather a good effect.

EXAMPLE 8

Contact action against *Musca domestica*

The test was carried out in a Petri dish. 1 ml of a 1000 ppm acetonic solution of active ingredient to be tested is pipetted on each of the two halves. After evaporation of the solvent 10 immobilized flies (cooling of the test individuals in a test tube in crushed ice) were put on the bottom of the dish whereupon the lid was put on. Within a few minutes all of the flies were back to normal. Control took place after one hour and the results are given below as the knock down effect in per cent.

| Compound | knock down effect |
| --- | --- |
| Example 1 | 100 % |
| Example 2.1 | 100 % |
| Example 2.2 | 100 % |
| Example 4 | 90 % |

EXAMPLE 9

Action against spider mites (*Tetranychus urticae*)

12 hours prior to the testing treatment dwarf bean plants (Phaseolus vulgaris) in the two-leave stage were infested with cultured mites. At the time of spraying the plants with an 800 ppm emulsion of active ingredient by means of a chromatographic atomizer all possible living stages of mites were found on the plants. The evaluation was made after 2 and 7 days.

| Compounds | killing in % after | |
| --- | --- | --- |
|  | 2 days | 7 days |
| Example 1 | 80 | 100 |
| Example 2.1 | 80 | 80 |
| Example 2.2 | 60 | 80 |

EXAMPLE 10

Action against midges (*Aedes aegypti*)

A 10 ppm solution of active ingredient in aceton was prepared and 1 ml thereof pipetted on the bottom of a Petri dish of 11 cm of diameter the total amount of active ingredient applied thus being 0.01 mg. After the evaporation of the solvent 10 female midges were exposed to the action of the active ingredient. The test was repeated four times at a temperature of 21° to 23°C with the following results.

40 killed midges (four times 10 midges) are indicated as 100%.

| Compound | killing effect after 3 hours |
| --- | --- |
| Example 1 | 100 % |
| Example 2.1 | 100 % |
| Example 2.2 | 100 % |
| Example 4 | 100 % |

EXAMPLE 11

Action against bugs (*Cimex lectularius*)

This test was carried out according to the statement in Example 10 with the following exceptions: the acetonic solution (1 ml of a 10 ppm solution of active ingredient) was applied to filterpaper which was placed on the bottom of a Petri dish of 9 cm of diameter. Ten adult bugs were put on the paper and exposed for 48 hours to the action of the active ingredient. The test was repeated twice with the following results. 20 killed bugs (twice 10 bugs) are indicated as 100%.

| compounds | killing effect after 48 hours |
| --- | --- |
| Example 1 | 95 % |
| Example 2.1 | 100 % |
| Example 2.2 | 100 % |

EXAMPLE 12

Action against cockroaches (*Periplaneta americana* and *Blatta orientalis*)

A 5% dusting agent was prepared according to Example 6 using as carrier exclusively talcum. By mixing equal parts of dusting preparation and talcum a dilution series with progressive dilution was made in which every step contained half the quantity of active ingredient contained in the preceding step. Accordingly, the series thus made had a content of active ingredient of 5, 2.5, 1.2, 0.6, 0.3, 0.15, 0.08% which corresponds to an amount of 100, 50, 25, 12.5, 6.2, 3.1, 1.5 mg of active ingredient per $m^2$ when 2 g of dusting preparation are applied. The test was carried out on green filter paper by means of a bell-shaped application apparatus and an amount of dusting preparation which corresponds to 2 g per $m^2$ and was applied with compressed air. The test animals which were in the fifth larvae stage (L-5) were put on the treated paper surface. Evaluation took place 24 hours later and the results listed below indicate the minimum concentration necessary to provide a 100% killing effect within 24 hours.

| compounds | Minimum concentration in mg providing 100% killing within 24 hours | |
| --- | --- | --- |
|  | Periplaneta americana | Blatta orientalis |
| Example 1 | 1.5 | 6.2 |
| Example 2.1 | 1.5 | 25.0 |
| Example 2.2 | 6.2 | 12.5 |
| Example 1 | 6.2 | 25.0 |

We claim:
1. ortho-(1,3-Dioxan-2-yl)-phenyl-N-methylcarbamate.

* * * * *

UNITED STATES PATENT OFFICE
// CERTIFICATE OF CORRECTION

Patent No. 3,933,858  Dated January 20, 1976

Inventor(s) Erwin Nikles et al.

It is certified that error appears in the above-identified patent and that said Letters Patent are hereby corrected as shown below:

The term of this patent subsequent to December 25, 1990, has been disclaimed.

Signed and Sealed this

Sixth Day of July 1976

[SEAL]

Attest:

RUTH C. MASON
Attesting Officer

C. MARSHALL DANN
Commissioner of Patents and Trademarks